US006669963B1

(12) United States Patent
Kampinga

(10) Patent No.: US 6,669,963 B1
(45) Date of Patent: Dec. 30, 2003

(54) STABLE PARTICLE IN LIQUID FORMULATIONS

(75) Inventor: Jaap Kampinga, Groningen (NL)

(73) Assignee: Elan Drug Delivery Limited, Nottingham (GB)

( * ) Notice: Subject to any disclaimer, the term of this patent is extended or adjusted under 35 U.S.C. 154(b) by 0 days.

(21) Appl. No.: 09/380,485

(22) PCT Filed: Mar. 18, 1998

(86) PCT No.: PCT/GB98/00817

§ 371 (c)(1), (2), (4) Date: Nov. 4, 1999

(87) PCT Pub. No.: WO98/41188

PCT Pub. Date: Sep. 24, 1998

(30) Foreign Application Priority Data

Mar. 18, 1997 (GB) .............................................. 9705588

(51) Int. Cl.[7] .................................................. A61K 9/14

(52) U.S. Cl. ....................... 424/499; 424/484; 424/489; 424/500; 424/501; 424/502; 435/91.53; 514/2; 426/103

(58) Field of Search ................................ 424/489, 499, 424/502; 435/91.53; 514/2

(56) References Cited

U.S. PATENT DOCUMENTS 3,970,765 A * 7/1976 Pitchon ...................... 426/534
4,031,255 A * 6/1977 Malizia ...................... 426/534
4,045,583 A * 8/1977 Jeffery ........................ 426/241
5,762,961 A 6/1998 Roser et al. ................ 424/464
5,766,520 A 6/1998 Bronshtein .................. 264/4.6
5,955,448 A 9/1999 Colaco et al. ................ 514/53
5,958,455 A 9/1999 Roser et al. ................ 424/489
6,008,187 A * 12/1999 Yang et al. ................. 424/409
6,290,991 B1 * 9/2001 Roser ......................... 424/502

FOREIGN PATENT DOCUMENTS

WO WO 96/03978 2/1996
WO WO 96/40077 12/1996
WO WO 97/28789 8/1997

OTHER PUBLICATIONS

Allen, J. Pharm. Sci. 66, 494–497, 1997.*
Meshali, Pharm. Acta Helv. 58, 62–64, 1983.*

* cited by examiner

*Primary Examiner*—Christopher S. F. Low
*Assistant Examiner*—David Lukton
(74) *Attorney, Agent, or Firm*—Morrison & Foerster LLP

(57) ABSTRACT

A stable particle in liquid formulation comprising a discontinuous phase of microparticles is suspended in a continuous phase which is a non-aqueous liquid, preferably biocompatible in which the microparticles are insoluble. The microparticles comprise finely powdered sugar glass, such as trehalose, palatnit, glucopyranosyl sorbitol, glucopyranosyl mannitol, lactitol and monosaccharide alcohols, such as mannitol and inositol, holding at least one biomolecular product, the biomolecular product in the sugar glass either being in stable solid solution or being itself in suspension in the sugar glass.

30 Claims, 8 Drawing Sheets

STABLE PARTICLE IN LIQUID FORMULATIONS

All living organisms require water. Indeed, to a large extent, most creatures are water. One of the few unifying themes in biology is that water accounts for about 75% of an organism's weight. Yet, remarkably, there are a number of creatures which can survive in a dry state after losing almost all of their water. This ability, called anhydrobiosis ("life without water"), is found across all biological kingdoms, including bacteria, fungi, animals and plants, and probably evolved at least two billion years ago. Such anhydrobiotic organisms are able to dry out completely and apparently die, yet they are not dead; they survive, inert and lifeless for indefinite periods in a state of suspended animation, until brought back to life by the presence of water. All these living things have solved the problem of how to preserve biological molecules without refrigeration or freezing.

A clearly defined characteristic which is common to anhydrobiotic organisms, and which is probably crucial to their desiccation tolerance, is their ability to make large amounts of a simple sugar. The most effective is trehalose (α-D-glucopyranosyl α-D-glucopyranoside) but the anhydrobiotic plant Craterostigina plantagineum for example accumulates sucrose rather than trehalose. It is clear that intracellular and extracellular sugars are necessary for the viability of dried cells or organisms. That trehalose alone can be sufficient for anhydrobiosis is confirmed by work in which the disaccharide has been artificially introduced into living cells, allowing them to be dried and rehydrated successfully.

Trehalose derives its stabilising ability from a combination of several properties. Like many other sugars, it can replace structural water by hydrogen-bonding with molecular surfaces. Trehalose is inert and cannot react with other molecules in the dry state. Certain other analogues are also stable and inert but most sugars react with amino groups (the so called Maillard reaction) at temperatures above freezing and destroy the product. When molecules are dried from a sugar solution using the correct procedure, a glass is formed in which molecules become embedded, minimising molecular diffusion and any associated degradation.

Many sugar solutions can behave in two very different ways upon drying. The commonest behaviour is that the sugar crystallises. Molecules in solution with the sugar are not protected when this occurs, since they are excluded from the crystals. The alternative behaviour is that the solution progressively becomes more concentrated until it is so viscous that it forms a solid glass at room temperature. When this happens, the biomolecular product has undergone a smooth change from being in liquid solution at the beginning to being in solid solution in the glass at the end. In this state the molecules of product can be visualised as embedded and tightly immobilised in the glass matrix. This is analogous to the ancient insects which are found embedded in fossil amber in a perfect state of preservation.

Since sugar glass is water soluble, the process is easily reversed in water so that the product smoothly goes back into its native state in liquid solution. These smooth, transitions ensure that there is no product damage during drying. As far as the product is concerned, the transition from liquid solution to solid solution is imperceptible. Because glasses of the best sugars are inert and have a high melting point when dry, the product is also protected on storage, even under hostile conditions.

Parenterally administered drugs are conventionally injected through a hollow metal needle as a solution in water containing buffer salts. Injections may be intradermal, subcutaneous, intramuscular or intravenous. More rarely another route such as intrathecal or intraocular may be appropriate. Drugs have been administered in this traditional way for over 100 years and in spite of the fear, pain and risk of infection associated with injections there has not been any major generally accepted improvement in the process in that time.

The liquid jet injector, which works by firing a very thin stream of liquid directly through the skin under very high pressure, achieved some success in vaccination programs but early models were unreliable. More recent developments such as the Mediject and Bioject devices have found significant niche applications in diabetes their uses and are being extended into other areas. However, a major disadvantage of the present technology is shared both by syringe and needle and by jet injector technology. Many parenteral drugs are unstable in aqueous solution and are manufactured and stored as a more stable freeze-dried cake or as a powder which requires reconstitution with water or buffer just before injection. This extra step demands training in the technique and adds risks in the form of inaccurate dispensing of solvent and therefore of dosage, or the introduction of infection by non-sterile technique. Drugs which are stored as a solution or a suspension (such as insulin) require refrigeration to prevent degradation and have a limited shelf life.

Reconstitution of dry drugs must be done correctly and precisely to ensure correct dosage and any errors in this step can be dangerous and, with highly potent drugs, can even be fatal. Often it is necessary to give more than one drug at a time. This may require multiple painful injections because certain drugs cannot be mixed in the one syringe as there are chemical incompatibilities between the molecules in solution which lead to loss of potency or even the generation of toxic reaction products.

The optimal solution to these problems which has long been a goal of drug formulation scientists is a stable liquid formulation that requires no reconstitution with solvent before injection. Although some minor improvements in aqueous solution stability have been achieved they do not provide the very high levels of drug stability which can be obtained with modern dry formulations using trehalose or similar stabilising excipients. However these latter preparations although extremely stable, even under very hostile environmental conditions, still require reconstitution before injection. They are also only stable so long as they are very dry. The uptake of moisture even in small amounts can render these dry preparations unstable on storage. They are usually stored as two-phase systems in which the drug is in the discontinuous solid chase and the continuous fluid phase is dry air, often under reduced pressure, or dry nitrogen, in a sealed glass vial.

Of the two main problems with existing vaccines for jet injection, instability on storage and the need to reconstitute dried vaccines, the former is solved by a drying process now patented by Quadrant Holdings Cambridge Ltd. using the simple sugar trehalose. Trehalose-dried vaccines can be stored at ambient temperatures of at least 45° C. without detectable deterioration. Most remarkably, even the aluminium hydroxide adjuvant gels are stabilised by trehalose during drying and storage and regain their full hydrated volume and function without clumping or precipitation.

Although the instability problem is addressed by this drying process, the previously described trehalose-dried vaccines were in the form of a solid glass foam and required reconstitution (for example with sterile water or buffer solution) before injection by conventional needle and syringe technology. Dry vaccines can be formulated in powder form and can be delivered through the skin using hypersonic shock waves of gas. Because of limitations of gas velocity and consequent penetrating power, there is some doubt as to whether deep intramuscular injections can be achieved by these means. A more useful formulation would be a ready to use stable liquid which did not require the transport of separate buffer solutions or reconstitution in the field yet which still had the extraordinary stability of trehalose-dried material. Such a vaccine could be formulated in multi-dose containers and delivered conveniently in mass immunisation campaigns by standard jet-injectors. We now describe a development using fine powders and non-aqueous vehicles in which the powders can be smoothly distributed as a stable monodisperse suspension.

Based on the phenomenon of anhydrobiosis, we have devised and validated processing conditions which ensure the formation of stable glasses which fully mimic the anhydrobiotic phenomenon. They can be used for stabilisation and preservation of most types of molecules and biological systems, including many vaccines, without the need for freeze-drying or refrigeration.

We now describe a process which can be used for formulating even the most unstable of drugs in a liquid formulation that is as stable as the best trehalose-dried formulations but has all the safety and convenience of ready to use liquid preparations.

A drug may be dried as a fine powder under conditions which ensure its optimal stabilisation in trehalose or other stabilising excipient in the glass state. Other sugars which spontaneously form good stabilising glasses are palatinit (a mixture of glucopyranosyl sorbitol and glucopyranosyl mannitol made by reducing palatinose (isomaltulose) with Hydrogen and Raney nickel catalyst: produced by Sudzucker A G in Germany). The pure isomers glucopyranosyl sorbitol and glucopyranosyl mannitol are also good, as is Lactitol (the reduced product of lactose or milk sugar). (Ref: (i) Colaco C. A. L. S., Smith C. J. S., Sen S., Roser D. H., Newman Y., Ring S. and Roser B. J. Chemistry of protein stabilisation by trehalose in "Formulation and delivery of proteins and peptides" Cleland and Langer eds American Chemical Society Washington 222–240 (1994); (ii) PCT application No. WO 91/18091 "Stabilisation of biological macro-molecular substances and other organic compounds". Roser B. J. and Colaco C.; (iii) U.S. Pat. No. 5,621,094 "Method of Preserving Agarose Gel Structure During Dehydration by Adding a Non-reducing Glycoside of a Straight Chain Sugar Alcohol" Roser B. and Colaco C.; (iv) PCT application No. WO 96/05809 "Improved method for stabilisation of biological substances during drying and subsequent storage and compositions thereof" Colaco C. Roser B. J. and Sen S.).

We have also found that a whole class of monosaccharide alcohols stated in the prior art to be useless as glass forming excipients can indeed form excellent stable formulations if correctly formulated. These include mannitol and inositol.

The formation of dry glass powders containing stabilised actives can be accomplished using any suitable sugar or sugar derivative from these groups. This may be achieved directly by spray drying or by some other drying process including standard processes like vacuum or freeze drying followed by a grinding step such as jet-milling, to reduce the dried formulation to a fine powder. This fine powder of sugar glass (discontinuous phase), containing the drug in a stable solid solution in the glass, is then formulated as a suspension in a two phase system containing, as the continuous phase, a biocompatible non-aqueous liquid in which the sugar is insoluble. The exclusion of water from this system preserves the stabilising effect of the trehalose or other stabilising excipient used. We have previously reported that trehalose-dried actives remain stable for several days in non-aqueous liquids in which the trehalose itself is insoluble. Gribbon E. M., Sen S., Roser B. J. and Kampinga J. Stabilisation of Vaccines Using Trehalose (Q-T4) Technology. In F. Brown (ed) New Approaches to Stabilisation of Vaccine Potency Dev Biol Stand Karger Basel 87 193–199 (1996). Providing the non-aqueous vehicle is stable and providing the preparation does not absorb significant amounts of water, it seems probable that such formulations would be as indefinitely stable as the trehalose-dried material itself. While experiments using non-aqueous laboratory solvents like acetone or dichloromethane establish the principle of the stability of active molecules in suspended sugar glass microspheres, such preparations are, of course, not injectable because the vehicle is toxic. There are, however, various non-aqueous vehicles which are approved by the regulatory authorities for parenteral injection and which have demonstrated safety and convenience. The liquid phase can be any injectable hydrophobic solvent such as an injectable sesame, arachis or soya oil, ethyl oleate or a water miscible non-aqueous solvent like polyethylene glycol. Since most of the suitable non-aqueous liquids are themselves very stable at room or elevated temperatures and do not need refrigeration, the resulting two phase preparation is inherently stable.

However, the fine particles of sugar glass have an inherent tendency to form clumps in many non-aqueous liquids because of phase separation. Since the sugar glass is intensely hydrophilic, the particles have a strong tendency to be excluded from a continuous hydrophobic phase and are forced together in clumps. These aggregates settle out of suspension and cannot be readily reconstituted as a monodisperse suspension by shaking or sonication. This leads to non-uniformity of drug dosage in the suspension and in the worst cases the formulation is not injectable due to large clumps which can block the needle. Although the ideal suspension is anhydrous or nearly so, we have found that surprisingly simple procedures derived from the field of stabilisation of water in oil (WIO) emulsions, can produce a smooth, monodisperse single-particle suspension of microspheres in a non-aqueous liquid.

Although the water content of these systems are very low (<1%), surfactants which are usually used to stabilise water in oil (WIO) emulsions have a dramatic effect at about 0.01% to 10%, preferably about 1%. They reduce the aggregates of glass particles back to a smooth monodisperse suspension which shows essentially no tendency to re-clump. These surfactants, which have either a low or very low Hydrophilic Lipophilic Balance (HLB), are themselves insoluble in water but are lipid soluble. Low HLB surfactants such as sorbitan sesguioleate (Arlacel C, HLB=3.7), mannide monooleate (Arlacel A,HLB=4.3), sorbitan tristearate (Span 65, HLB=2.1) and glycerol monostearate (Arlacel 129, HLB=3.2) have very low toxicity (oral $LD_{50}$ in rats >15 g/kg), are already used clinically in WIO emulsions such as Freund's adjuvant for injection and are also approved by the regulatory authorities for this purpose.

Preferably, the surfactant is added to the continuous non-aqueous liquid phase before addition of the powder particles.

Arlacel A is an essential component of the so called "Freund's adjuvant" which is widely used in immunising animals to produce maximum titres of serum antibodies. (Ref: Handbook of Experimental Immunology $4^{th}$ Edition Eds D M Weir, Co-editors L. Herzenberg and L Herzenberg Vol 1 p 8.10 (1986)). Freund's adjuvant is basically a fine water in oil emulsion in which the antigen is dissolved in the discontinuous water phase while the continuous phase of light paraffin oil acts as a reservoir from which the antigen is slowly released. Complete Freund's adjuvant also contains heat-killed Mycobacterium tuberculosis which causes violent inflammation, enhancing the responsiveness of the immune system. This precludes its use in humans.

A major difference between a fine water in oil emulsion like Freund's adjuvant and the monodisperse glass in oil suspensions described here is the relatively low dispersion energy required to produce the latter. While dispersion of the aqueous phase as fine droplets in a WIO emulsion requires prolonged and vigorous mixing (a high speed homogeniser is used to produce Freund's adjuvant and it is usually run for 15 to 30 minutes at top speed of >18,000 RPM before a stable emulsion is achieved) the stable suspensions described herein require only the addition of the finely powdered drug to the oil/surfactant base and a vigorous shake to mix the phases. A brief <5 min exposure to an ultrasonic bath can be used to ensure the break up of any small clumps which may have formed before or during addition to the hydrophobic phase.

Providing the fine microspheres of sugar glass are completely insoluble in the hydrophobic solvent, they are stable in the glass phase with no tendency to re-crystallise and the stabilised molecules in solid solution in the glass spheres are also stable.

A significant disadvantage of powders produced by conventional spray drying technology is the wide variation in particle size usually produced. In addition, conventional spray dryers have great difficulty in producing particles with a mean diameter significantly smaller than 5–10$\mu$. Particles of this size sediment quickly in low viscosity liquids. This can lead to large variation in dose distribution within the vial and a requirement for frequent and vigorous shaking to re-suspend the particles. Particles of sugar glass of about 0.1 to 1$\mu$ diameter would be better as they are maintained in even suspension by normal thermodynamic forces such as Brownian motion. While standard pharmaceutical processing techniques such as jet milling can reduce the size of powders to a mean diameter of around 1 to 2$\mu$, it is not usually practicable to go much below this. An additional step such as jet milling would, of course add to the cost of processing.

By using ultrasonic nebulisers instead of conventional spray nozzles, it is possible to modify spray drying equipment to yield small and very uniform microspheres. There seems to be no reason why this process should not be adapted to sterile processing of stabilised vaccines in large quantities. One disadvantage of reducing the particle size to sub-micron dimensions in air or a continuous phase of some other gas, is the losses of material often experienced because of the difficulty of separating the fine particles from the gas stream. Alternatively, standard pharmaceutical high pressure microhomogenising equipment such as the Microfluidizer (Constant Systems Inc.) which is widely used to produce sterile, stable microemulsions is also efficient in producing stable microsuspensions by reducing the mean size of particles suspended in a continuous liquid phase. This process gives virtually total recovery of material and is probably the method of choice particularly for rare or expensive actives. A single step such as this could be inexpensively incorporated into the production process as production costs are around $1,000 per Kilogram of powder. This would contain around 20,000 doses of a standard childhood vaccine such as DTP, adding 5 cents to the cost of each dose. Since losses of the current unstable vaccines can be 50% to 90% in the field even with the expensive cold chain (refrigeration) in place, the additional cost of stable liquid vaccines, which could do away with the cold chain, would be quickly recouped.

SUMMARY OF THE INVENTION

The present invention provides a process for producing stable particle in liquid (PIL) formulations together with the products of the processes. The particles are in fine powder form, preferably being microparticles of 10 microns diameter or less, most preferably 1 micron or less. Preferably the particles do not exhibit a wide variation in particle size. The particles are essentially dry, having a very low water content of less than about 1%. The particles may contain one or more biomolecular product and may contain other additives, excipients and the like. The biomolecular product is preferably a drug or other biologically active ingredient such as a protein, antibody, enzyme (e.g. restriction endonuclease) and the like, but does not exclude other biological materials (e.g. foodstuffs, dye stuffs, beverages and the like) The particles are suspended in a non-aqueous liquid in which they are insoluble.

According to the invention there is provided a formulation of fine dry powder particles which comprise a biomolecular product, the particles constituting a monodisperse suspension in a continuous phase of a bio-compatible non-aqueous liquid in which the particles are not soluble, wherein the continuous phase may include a low HLB lipid-soluble surfactant.

The suspension formulation may, for example, contain from about 1% to more than 50%, e.g. 10%, particulate product although a loading of more or less may be preferred depending on the chosen application and the chosen ingredients of the mixture.

The particles comprise or consist of molecules of the product in a sugar glass. The product in the sugar glass is either in stable solid solution or is itself in suspension in the sugar glass. Preferably the sugar glass is formed from trehalose.

In this application the term "sugar" is to be understood as covering not only disaccharide sugars such as trehalose, but also monosaccharide sugars and their non-reducing derivatives such as sugar alcohols including mannitol, inositol, xylitol, ribitol and the like, which form a general class of stabilising glass-forming sugars and sugar derivatives. The term "sugar glass" is to be understood as covering not only glasses which are readily and rapidly dissolved in an aqueous environment such as trehalose glass, but also sugar glasses in which the sugar molecule has been modified by the attachment of one or more hydrophobic side chains to make the glass more slowly soluble in body fluids than the native sugar in order to give controlled release of a biomolecular product.

Where the formulation is intended for medicinal use, e.g. as an injection formulation, the non-aqueous continuous phase liquid must be bio-compatible. The liquid phase may be an injectable hydrophobic solvent or a water miscible non-aqueous solvent. Since sugar glass stabilisation of the biomolecular product is utilised, it is clear that the non-aqueous liquid must be a non-solvent for sugar. For example any non-aqueous non-toxic oil approved for parenteral use could be employed in the invention. A low viscosity oil such as ethyloleate is suitable and has the advantage that it is easy to inject. Water miscible non-aqueous solvents include glycerol, ethylene glycol, propylene glycol, propylene oxide, polypropylene glycol.

The lipid soluble surfactant has a low or very low HLB. Those skilled in the art will readily appreciate the meaning of these general terms, particularly in the context of the HLB values given in the attached description relating to preferred examples of low HLB surfactants. It is a particularly surprising aspect of the present invention that a surfactant which would have been especially developed by the commercial manufacturer for stabilising water in oil emulsions would have any activity or utility whatsoever in formulating an essentially anhydrous preparation. The surfactants include sorbitan sesquioleate, mannide monooleate, sorbitan tristearate and glycerol monostearate, plus Lecithin (phosphatidyl choline) and also di-palmitoyl phosphatidyl choline, di-stearoyl phosphatidyl choline and di-myristoyl phosphatidyl choline as examples of normal body components with surfactant activity which are advantageously used in this technology. Also the synthetic and already approved surfactants such as Sorbitan laurate, palmitate, stearate and oleate.

By virtue of the invention it is possible to produce stable particle in liquid formulations in which fine dry powder is smoothly distributed as a stable monodisperse suspension. Those skilled in the art will readily appreciate that such monodisperse suspensions could be injected directly either by syringe and needle or by liquid jet injector. The formulations may be injected as such without requiring reconstitution with solvent before injection. This is clearly advantageous where the provision of sterile conditions and sterile reconstituting solvents and/or buffers is problematic. The particle in liquid formulations are stable and consequently it is possible to dispense with the need for refrigeration.

Solid solutions of anhydrous drug stabilised in sugar glass in fine particulate form are readily hydratable. It is a particular further advantage of the present invention that biocompatible formulations can be injected directly into a recipient with the effect that the normal physiological acueous environment will hydrate the drug in situ. It can readily be appreciated that a stable, temperature insensitive, directly injectable drug formulation has enormous potential in vaccination programmes and for widespread prophylactic or therapeutic drug administration.

The formulations of the invention can also be used for diagnostics and reagents if the non-aqueous liquid is water soluble or miscible. A liquid dispenser can then store unstable diagnostic reagents without refrigeration and dispense them into test systems which are water-based such as immunoassays, DNA probe based diagnostics, PCR reactions and the like. On contact with water in the diagnostic system, the finely powdered diagnostic reagent in the non-aqueous vehicle will instantly dissolve and the reagent will become fully active. As an example, this process can be used for restriction enzymes used to digest DNA at specific sequence sites.

The particles in a particular continuous phase preparation can be of more than one type which interact rapidly together when they are released in water. The example we give is alkaline phosphatase in one particle and p-nitropyenyl phosphate (its substrate) in the other. These could just as easily be the two pro-drug components which need to interact to produce an active drug from two pro-drugs. One can also have several different particles such as the individual components of a multivalent vaccine. These do not undergo destructive interactions in the oil and they do not have time to interact when they are rehydrated in the body because they are absorbed from the point of injection and transported to their site of action.

In the restriction enzyme example we can use multiple reagents in separate particles for complex molecular biology techniques such as the components of the Polymerase Chain Reaction (PCR) or sequencing reactions. In the former, one particle would contain the DNA polymerase, one would contain one primer and the third would contain the other primer and a fourth could contain the nucleotides. In a sequencing reaction the DNA polymerase could be in one particle and the nucleotides and di-deoxy chain terminating nucleotides in another. It is clear that the ability to mix different reagents in non-interacting particles in the oil opens up many possibilities for the design of powerful and convenient kits.

EXAMPLES

Example 1

Alkaline Phosphatase

Figure 1:
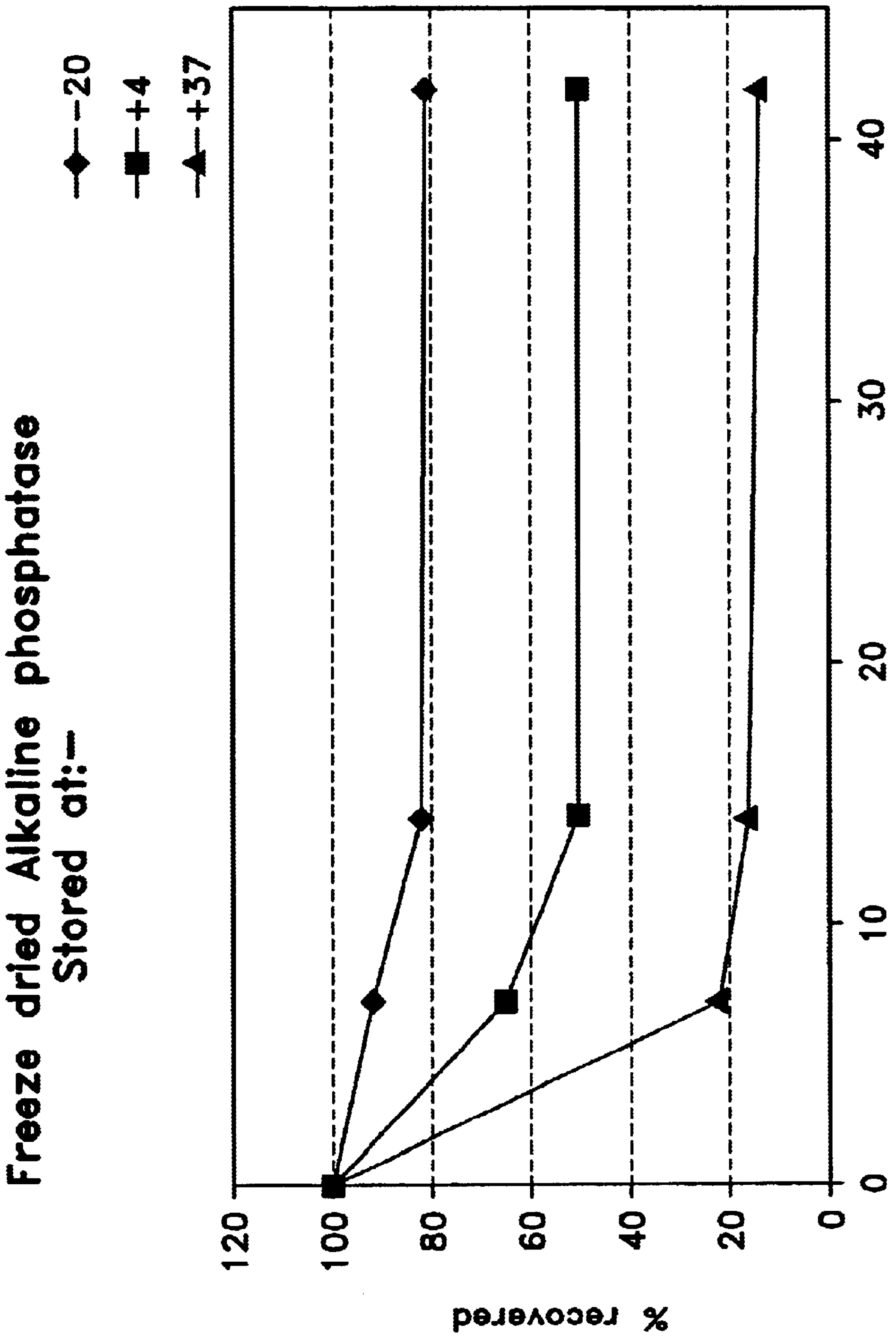
FIG. 1 shows the time-dependent activity of freeze-dried alkaline phosphatase at 37°, 4° C. and −20° C.

The enzyme Alkaline phosphatase from bovine intestinal mucosa EC number 3.1.3.1 (Sigma-Aldrich Co. Ltd. p8647) is usually obtained as a freeze-dried powder. This requires storage desiccated in a freezer at <0° C. in order to preserve the activity of the enzyme. Even at this temperature the freeze-dried enzyme gradually loses activity. When stored at higher temperatures there is more rapid, temperature dependent loss of activity (FIG. 1).

Formulation and Drying

The enzyme was dissolved in a buffer composed of:

| Substance | concentration |
|---|---|
| Trehalose | 0.6M |
| Sodium sulphate | 0.35M |
| Bovine serum albumin | 0.75 mM |
| Alkaline phosphatase | 40 units/ml |
| Zinc chloride | 1 mM |
| Magnesium chloride | 1 mM |

and dried in a Labplant SD1 spray dryer. Drying conditions were: inlet temperature 135° C. outlet temperature 80° C. with a maximum airflow. The residual water content of the glass powder at the end of this process was measured to be 2% by Thermogravimetric analysis (TGA) on a Seiko SSC/5200 machine (Seiko Instruments Inc.).

Storage

Aliquots of 100 mg of the powder were weighed into 5 ml vaccine vials and sealed under vacuum. Other aliquots were weighed into vials and resuspended in pharmaceutical grade ethyl oleate (Croda Chemical Company Ltd.) at a concentration of 200 mg/ml oil. These vials were also sealed under vacuum. Samples of both the dry powder and the oil suspension were then stored for various periods of time at either 37° C. or 55° C.

Assay

At the end of the storage period 5 ml volumes of buffer of the following composition, adjusted to pH 10.0 with sodium hydroxide solution,

| Substance | concentration |
|---|---|
| Glycine | 100 mM |
| Zinc chloride | 1 mM |
| Magnesium chloride | 1 mM |

were added and the vials centrifuged at 3,500 RPM for 10 min in a IEC Centra 413 centrifuge. This had the effect of transferring the glass particles containing the enzyme through the oil water interface and dissolving them in the buffer to recover the residual enzyme. The amount of enzyme recovered was identical whether or not the vials were shaken vigorously after the addition of the aqueous buffer. The activity was measured using a kinetic procedure for determination of "Glycine units" (Sigma-Aldrich Co Ltd.) on a Shimadzu UV-160A Spectrophotometer at 37° C. using p-nitrophenyl phosphate substrate and measuring colour development at a wavelength of 405 nm.

Results

Figure 2:
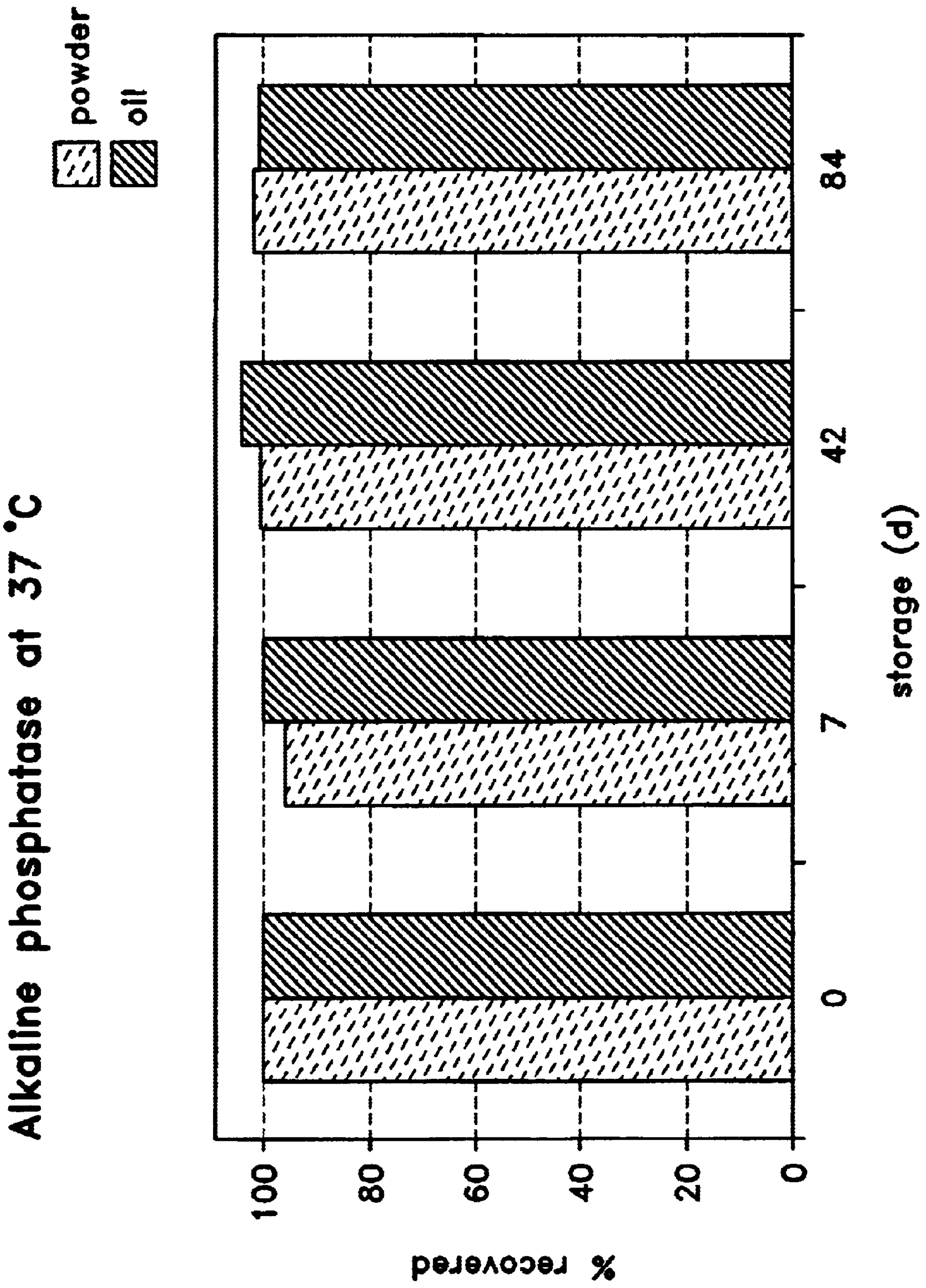
FIGS. 2 and 3 show the activity of dry powder or oil suspension formulations of trehalose stabilised alkaline phosphatase at 37° C. and 55° C.
Figure 3:
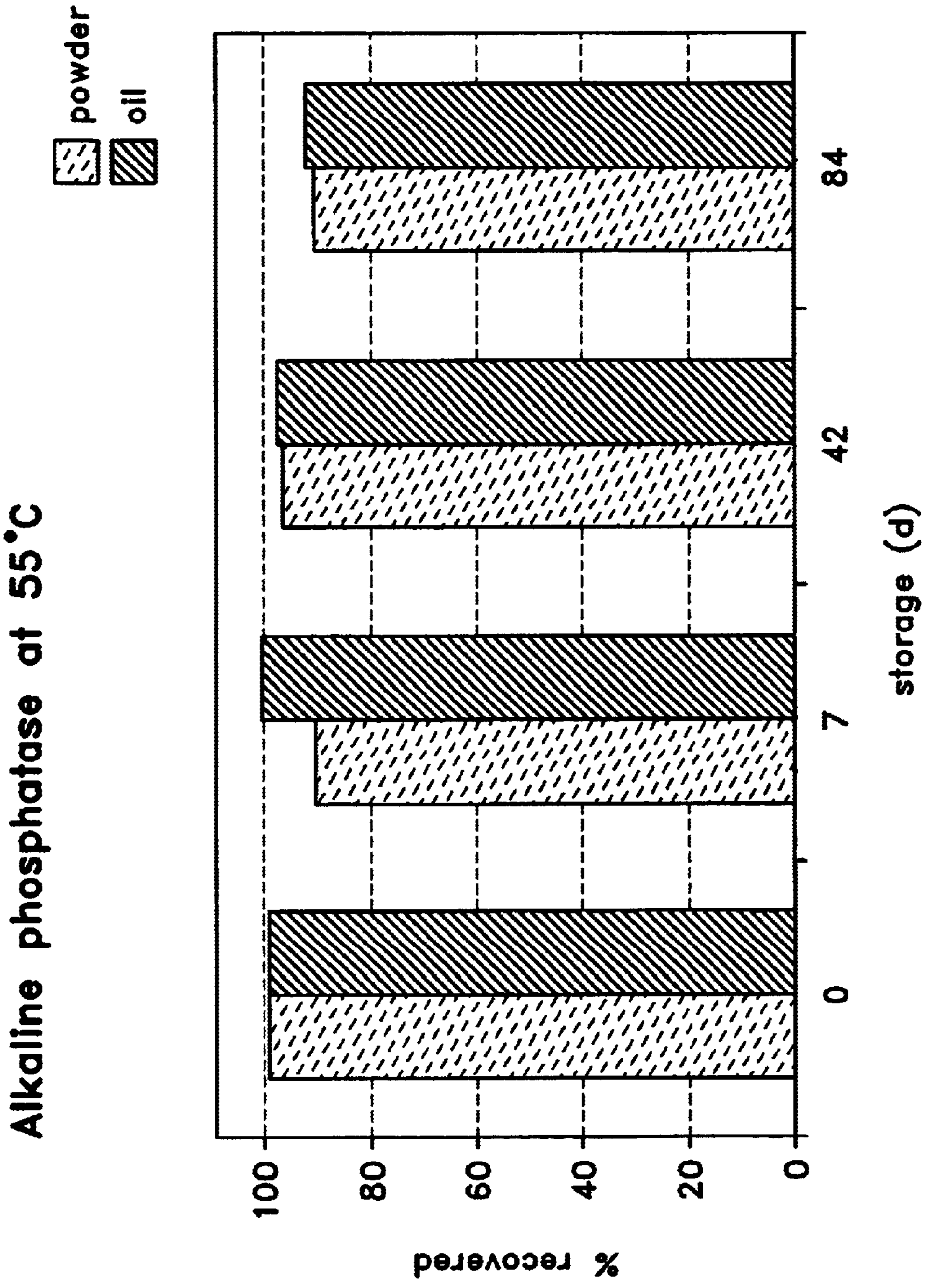

When stored at 37° C., there was no loss of enzyme activity over 84 days of storage in either the dry powder or the oil suspension. (FIG. 2). When stored at 55° C. there was a slight loss within the first 7 days but over 90% of the activity was again stable for up to 84 days (FIG. 3). Wherever there was a difference between the oil and powder samples the former was better but the difference was not significant. Essentially identical results were obtained whether mineral oil or ethyl oleate was used as the continuous phase.

In other experiments spray drying was done using different buffer compositions containing Calcium lactate in place of sodium sulphate or mannitol in place of trehalose. These gave essentially similar results. The good results with mannitol-based glass-forming buffers was particularly surprising as previously disclosed work had stated that it was not possible to use monosaccharide sugar alcohols as stabilising agents (PCT application No. WO 91/18091 "Stabilisation of biological macro-molecular substances and other organic compounds", Roser B. J. and Colaco C.; U.S. Pat. No. 5,621,094 "Method of Preserving Agarose Gel Structure During Dehydration by Adding a Non-reducing Glycoside of a Straight Chain Sugar Alcohol" Roser B. and Colaco C.; PCT application No. WO 96/05809 "Improved method for stabilisation of biological substances during drying and subsequent storage and compositions thereof" Colaco C. Roser B. J. and Sen S.). This is clearly not the case providing that the formulation and drying technique is such as to ensure that a good glass is formed.

As an indication of the inertness and stability of the actives dried in the glass powders in suspension, mixtures of powders containing alkaline phosphatase- and powders containing p-nitrophenyl phosphate- were made in mineral oil and stored at 55° C. for 7 days. These suspensions appeared unchanged at the end of this time. Upon addition of 1 ml of water and shaking, an intense yellow colour promptly developed in the separated aqueous phase indicating that the water had reactivated both the enzyme and the substrate. This result shows that these preparations can accommodate, in the same vehicle, components that would react together in conventional aqueous mixtures. This property should be of great value in multivalent vaccines for example. It has not escaped our notice that it is also a good model system for the development of so called "binary" drugs where the final active component is synthesised or released by a chemical reaction which only begins when the precursor molecules are wetted by body fluids.

Example 2

Recombinant Human Erythropoietin (EPO)

EPO was chosen as an example of a modern pharmaceutical which is produced by genetic engineering of a recombinant protein in *E coli.*

Freeze dried EPO was re-hydrated and diluted 100 fold with a buffer of the following composition:

| Substance | concentration |
|---|---|
| Trehalose | 0.6 M |
| Sodium sulphate | 0.7 M |
| Bovine serum albumin | 0.75 mM |

and dried in a spray dryer as above. The powder was weighed into 125 mg aliquots and subjected to secondary drying at a temperature ramping from 40° C. to 80° C. at a rate of 15 degrees per hour under vacuum and then either sealed in a serum vial or re-suspended in 0.5 ml of mineral oil BP and sealed. They were then stored at 37° C. or 55° C. for up to 15 days. At the end of the storage period, residual EPO was extracted into phosphate buffered saline containing 0.01% BSA as above and the amount remaining in the extract was measured using a Quantikine IVD EPO-specific immunoassay (RD Systems Inc).

Figure 4:
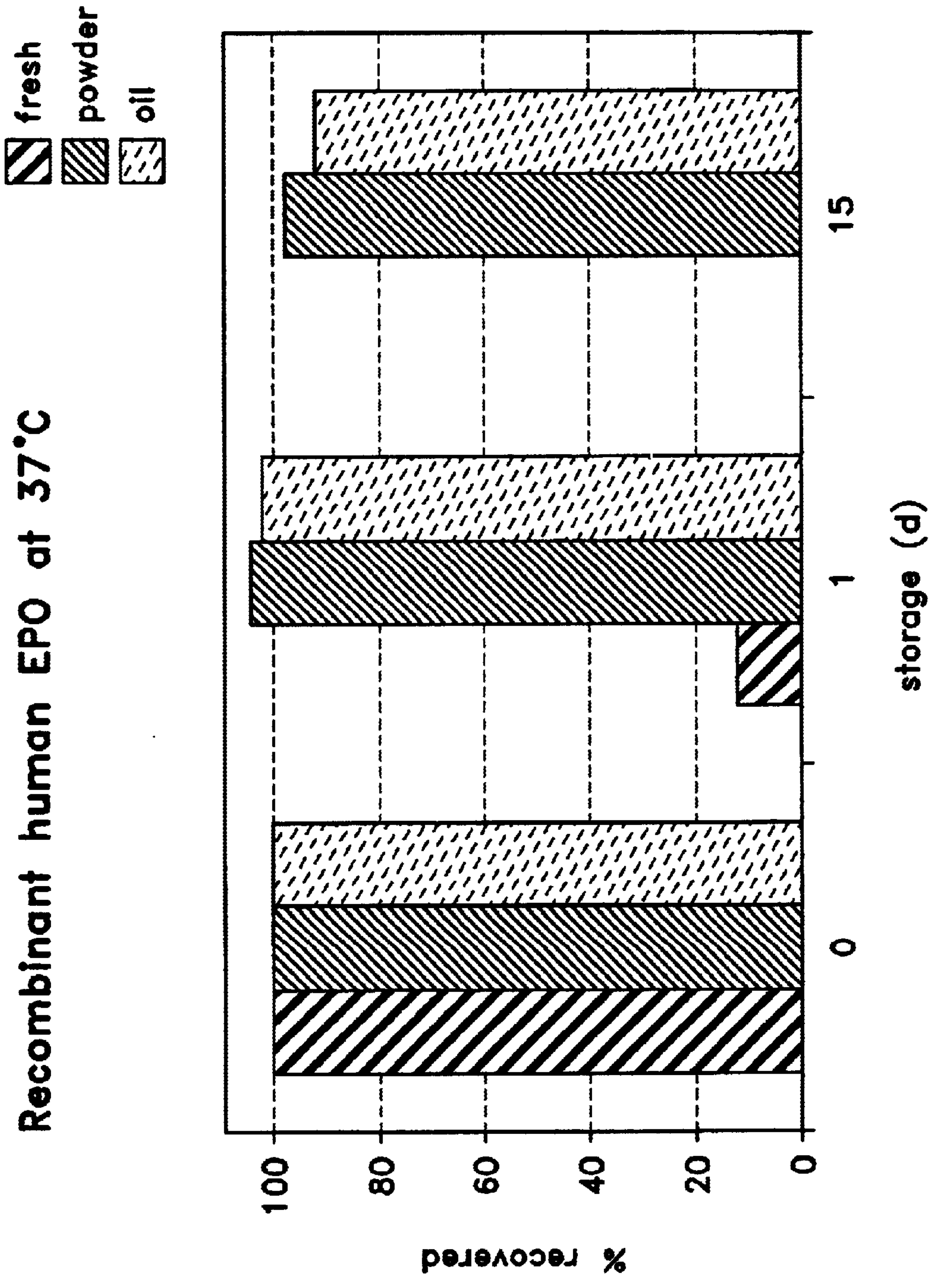
FIGS. 4 and 5 show the activity of freeze dried, and trehalose stabilised dry powder or oil suspension formulations of recombinant EPO at 37° C. and 55° C.
Figure 5:
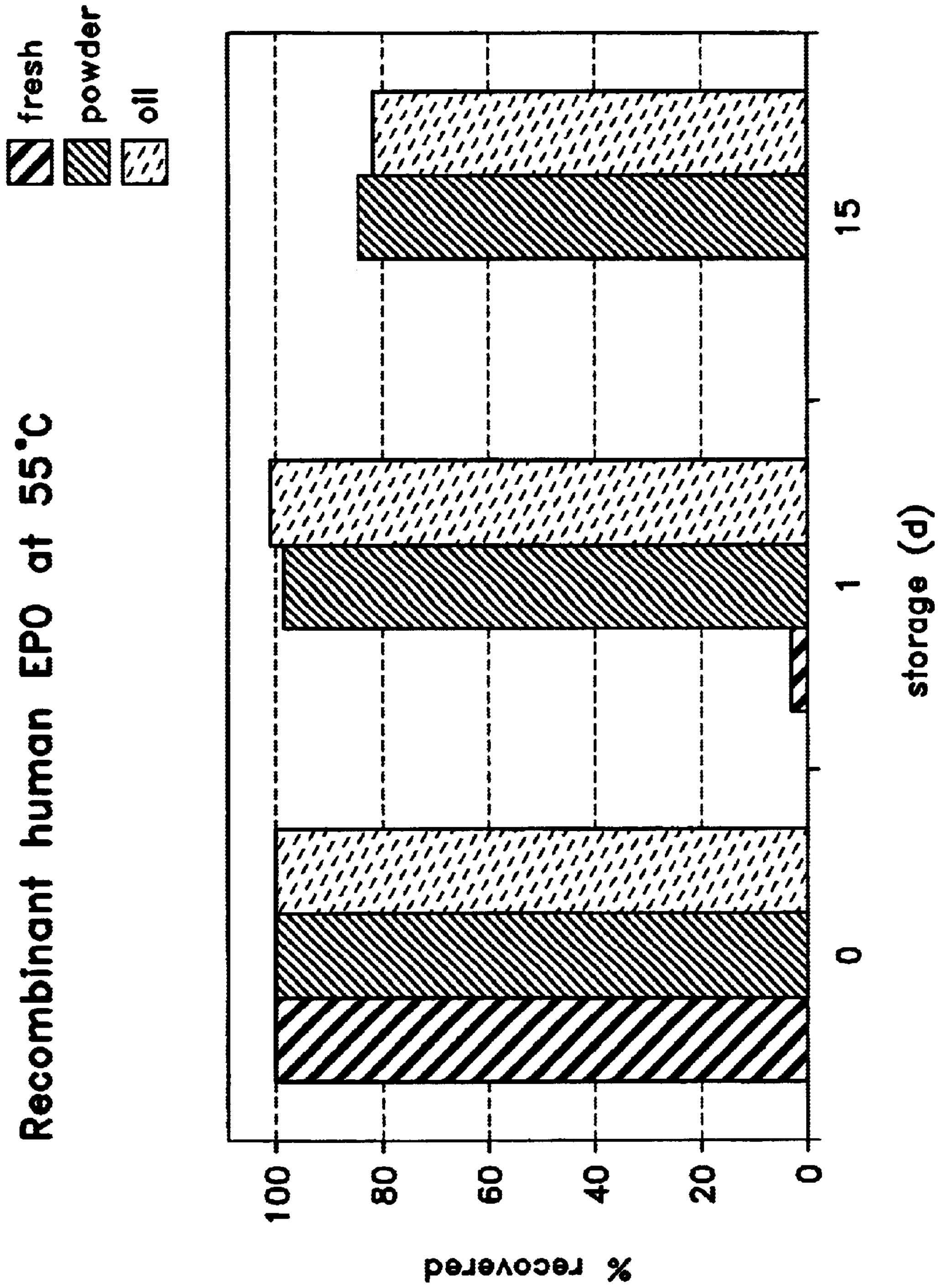

Within one day at 37° C. fresh EPO has lost 88% of its activity while the dried material, whether suspended in oil or not is fully active (FIG. 4). There is a small loss of activity by 15 days but more than 90% of activity remains. When stored at 55° C. fresh EPO loses >95% activity within one day (FIG. 5). In contrast, the dried material loses no activity in the first day and >80% activity can still be recovered 15 days later.

Example 3

Restriction Endonuclease EcoR1

Restriction enzymes are customarily stored in freezers at −20° C. in buffers containing 50% glycerol to prevent ice formation. Even under these conditions some of them have a limited storage life and need to be replaced at intervals. Several enzymes were dried using the technique of the present invention with similar results. The data with one enzyme, EcoR1, is illustrated. The enzyme solution was diluted 100 fold in SC buffer (Colaco C. A. L. S., Sen S., Thangavelu M., Pinder S. and Roser B. "Extraordinary stability of enzymes dried in trehalose: Simplified molecular biology." *Biotechnol.* 10 1007–1011 (1992)). The dried enzyme was produced in the spray dryer as above, sealed in vials with or without oil and its stability was compared with fresh liquid enzyme diluted in cutting buffer at three storage temperatures 4° C., 37° C. and 55° C. To determine residual activity after storage, the enzyme was recovered into the acueous phase as described earlier, diluted with SC buffer in a 2-fold dilution series and used to cut 0.5 μg of phage lambda DNA (Life Technologies Inc). The completeness of cutting at various dilutions was assessed by separating the DNA fragments by agarose gel electrophoresis in which the bands were visualised under UV light by ethidium bromide staining. The titre of the enzyme was expressed as the maximum dilution which showed complete cutting with no partial bands appearing.

Figure 6:
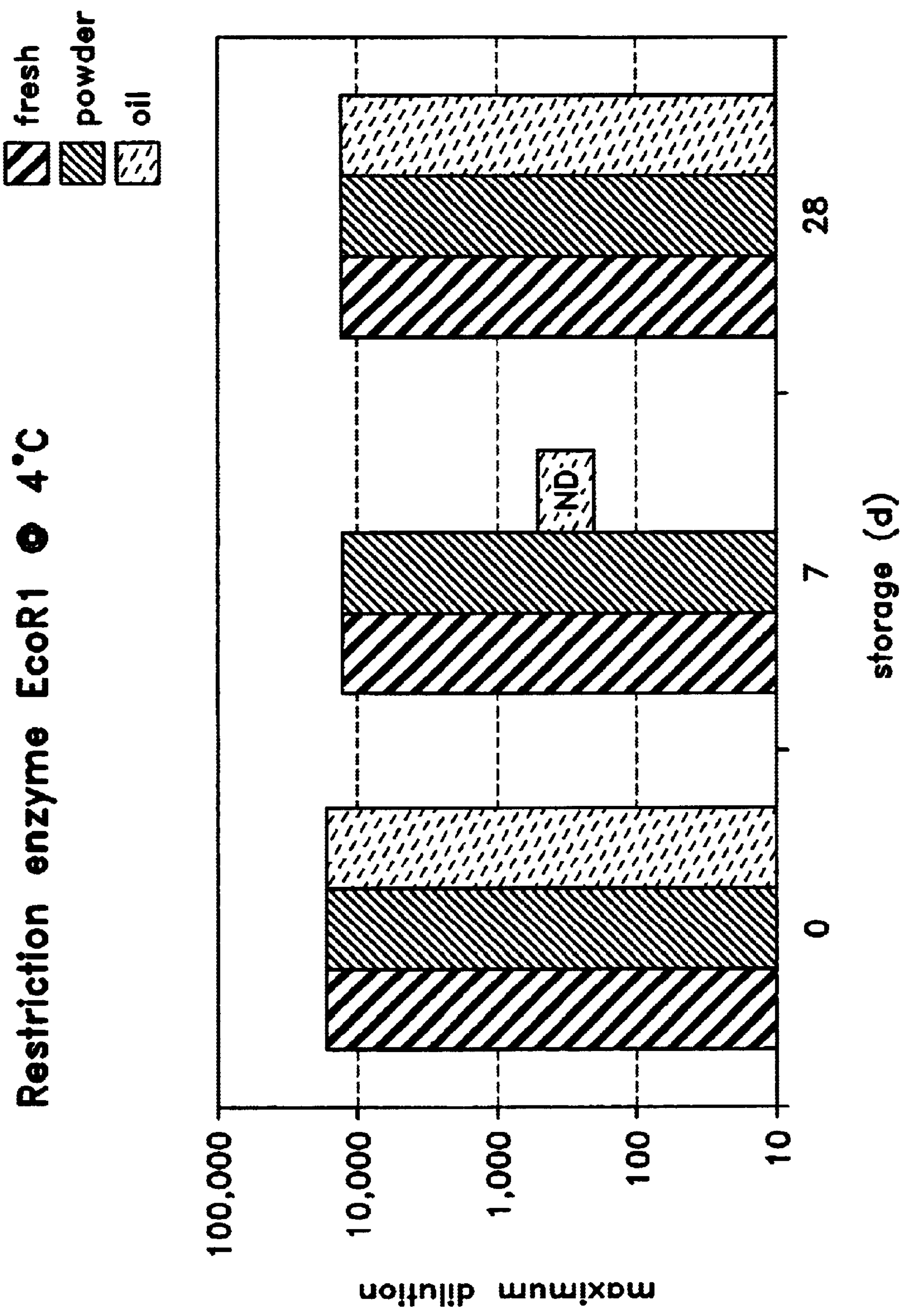
FIGS. 6, 7 and 8 show the activity of freeze dried, and trehalose stabilised dry powder or oil suspension formulations of EcoR1 at 4° C., 37° C. and 55° C.
Figure 7:
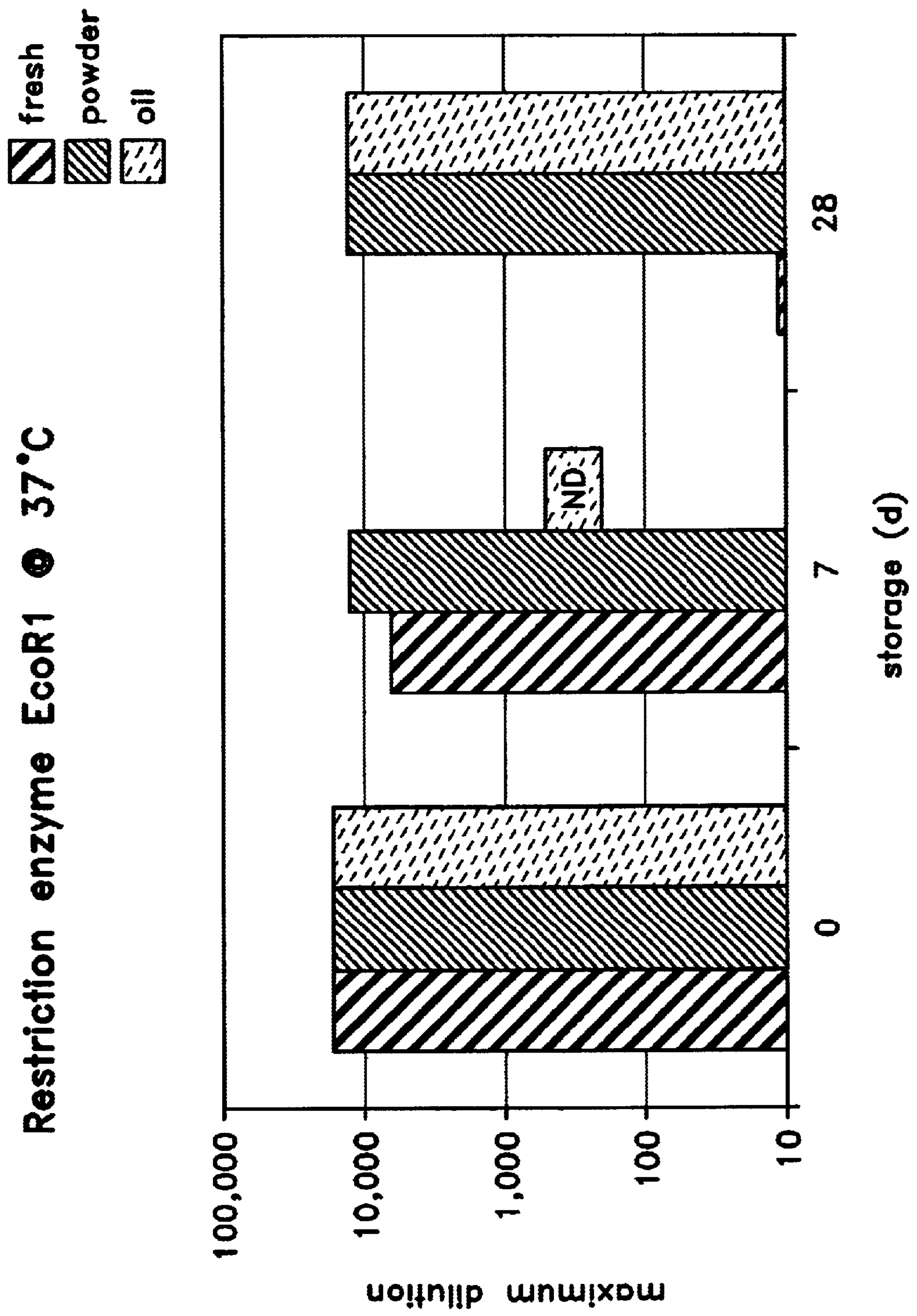
Figure 8:
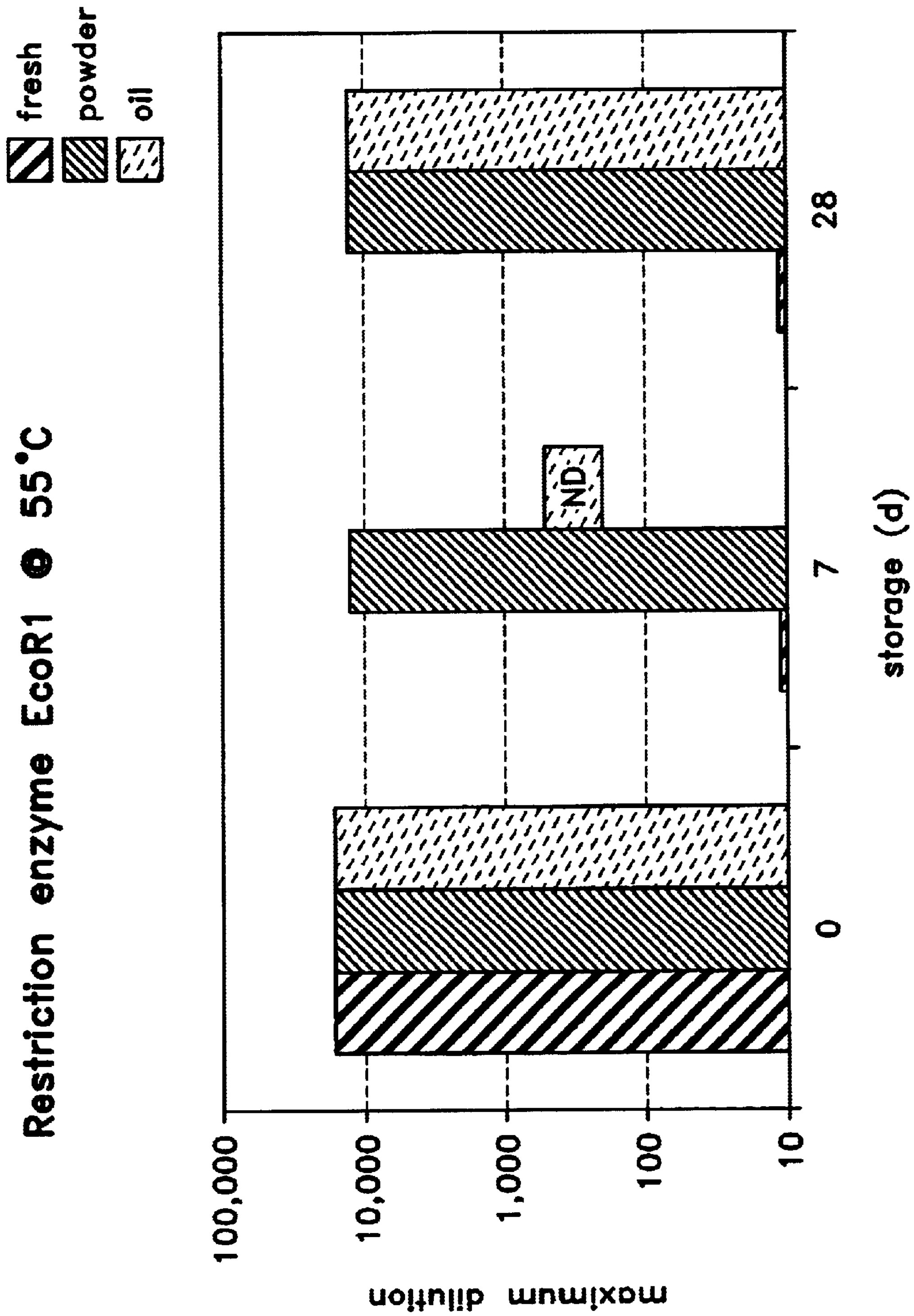

When stored at 4° C., none of the preparations showed progressive loss of activity over 28 days. Even the fresh liquid preparation was stable at this temperature (FIG. 6). At 37° C., the fresh enzyme lost essentially all activity by 28 days while the dried enzyme with or without added oil was highly active (FIG. 7). The dried preparations showed the same recovery of activity after storage at 55° C. while, at this temperature, the fresh enzyme was completely inactive within 7 days (FIG. 8).

These formulations of restriction enzymes provide a convenient new way to cut DNA. The oil containing suspended enzyme powder is overlaid on a solution of DNA, vortexed and centrifuged in an Eppendorf centrifuge. The suspension of enzyme dissolves in the aqueous phase containing the DNA and begins cutting at 37° C. The oil phase forms a convenient vapour barrier overlying the digest preventing evaporation. This process is already familiar to molecular biologists being a common part of the polymerase chain reaction technique. Room temperature storable restriction enzymes in a non-hygroscopic mineral oil vehicle constitutes a valuable and convenient new product for molecular biology.

What is claimed is:

1. A stable particle-in-liquid formulation comprising a discontinuous phase of microparticles suspended in a continuous phase which is a non-aqueous liquid in which the microparticles are insoluble, wherein the microparticles comprise finely powdered sugar glass holding at least one biomolecular product, the biomolecular product in the sugar glass either being in stable solid solution or being itself in suspension in the sugar glass.

2. A formulation according to claim 1 wherein the sugar glass is formed from one or more sugars selected from the group consisting of trehalose, palatinit (a mixture of glucopyranosyl sorbitol and glucopyranosyl mannitol), glucopyranosyl sorbitol, glucopyranosyl mannitol, lactitol, and monosaccharide alcohols.

3. A formulation according to claim 1 wherein the continuous phase is biocompatible.

4. A formulation according to claim 1 in which the continuous phase is a hydrophobic solvent.

5. A formulation according to claim 1 in which the continuous phase is water miscible.

6. A formulation according to any of claims 1 to 5 in which the sugar glass microparticles are of diameter from about 0.1 to about 10$\mu$.

7. A formulation according to claim 5 wherein the microparticles do not exhibit a wide variation in particle size.

8. A formulation according to any of claims 1 to 5 or 7 in which the microparticles are essentially dry.

9. A formulation according to any of claims 1 to 5 or 7 in which the biomolecular product is a drug or other biologically active ingredient.

10. A formulation according to any of claims 1 to 5 or 7 in which the microparticles constitute a monodisperse suspension in the continuous phase.

11. A formulation according to any of claims 1 to 5 or 7 which contains from about 1% to more than 50%, by weight microparticles in the discontinuous phase.

12. A formulation according to claim 1 in which the continuous phase includes or consists of at least one oil selected from the group consisting of sesame oil, arachis oil, soya oil, ethyloleate and mineral oil.

13. A formulation according to claim 1 wherein the non aqueous continuous liquid phase comprises or consists of a water miscible non aqueous solvent selected from the group consisting of polyethylene glycol, glycerol, ethylene glycol, propylene glycol, propylene oxide, and polypropylene glycol.

14. A process for producing a stable particle in liquid formulation of claim 1, which comprises the steps of:

(a) producing microparticles containing one or more biomolecular products held in a sugar glass, wherein the biomolecular products in the sugar glass are either (i) in stable solid solution or (ii) in suspension in the sugar glass;

(b) adding the microparticles to a non aqueous continuous liquid phase in which the microparticles are not soluble; and (c) forming a discontinuous phase of the microparticles suspended in the non aqueous continuous liquid phase comprising the stable particle in liquid formulation.

15. A formulation according to claim 1 which is a binary drug formulation wherein the biomolecular product is a drug precursor and wherein the final active drug component is synthesised or released by a chemical reaction which only begins when the precursor is wetted by body fluids after administration of the formulation to a patient.

16. A formulation according to claim 1, wherein one or more biomolecular products are suspended in the sugar glass.

17. A formulation according to claim 1 or 16 containing a mixture of microparticles which release more than one biomolecular product when contacted with an aqueous environment.

18. A formulation according to claim 17 wherein two or more biomolecular products interact when released in an aqueous environment.

19. A formulation according to any of claims 1 to 5 in which the sugar glass microparticles are less than 1$\mu$ in diameter.

20. A formulation according to any of claims 1 to 5 in which the biomolecular product is a biological material selected from the group consisting of a food stuff, a dye stuff, and a beverage.

21. The formulation according to any of claims 1 to 5 wherein the sugar glass comprises sugar molecules modified by attachment of one or more hydrophobic side chains, to permit controlled release of the biomolecular product.

22. The formulation according to claim 9 wherein the biologically active ingredient is a protein, antibody or enzyme.

23. The formulation according to any of claims 1 to 5 wherein the microparticles further comprise an additive or an excipient.

24. The stable particle-in-liquid formulation of claim 1, wherein the biomolecular product is a restriction endonuclease.

25. A method for cleaving deoxyribonucleic acid (DNA) comprising (a) combining a formulation according to claim 24 with an aqueous solution of DNA to produce a composition comprising an aqueous phase and a non-aqueous liquid, wherein the aqueous phase contains the restriction endonuclease and the DNA, and wherein the non-aqueous liquid is a hydrophobic solvent;

(b) incubating the composition of step (a) for a time and under conditions effective to cleave the DNA, thereby generating fragments of DNA; and (c) recovering the fragments of step (b).

26. The formulation of claim 1, further comprising a surfactant.

27. The formulation of claim 26, wherein the amount of surfactant in the continuous phase is from about 0.01% to about 10% by volume.

28. The formulation of claim 26, wherein the surfactant is at least one compound selected from the group consisting of sorbitan sesquioleate, mannide monooleate, sorbitan tristearate and glycerol monostearate, Lecithin (phosphatidyl choline), di-palmitoyl phosphatidyl choline, di-stearoyl phosphatidyl choline, di-myristoyl phosphatidyl choline, and sorbitan laurate, sorbitan palmitate, sorbitan stearate and sorbitan oleate.

29. The method of claim 14 wherein a monodisperse single-particle suspension of microparticles is produced in the non-aqueous continuous liquid phase by inclusion in the continuous phase of at least one surfactant having a low or very low Hydrophilic Lipophilic Balance (HLB).

30. The method according to claim 29 wherein the surfactant is added to the continuous non-aqueous liquid phase before addition of the microparticles.

* * * * *